(12) United States Patent
Gillis et al.

(10) Patent No.: US 7,648,496 B2
(45) Date of Patent: Jan. 19, 2010

(54) DEVICE AND METHOD FOR ACCURATE DELIVERY OF AN ACTIVE AGENT

(75) Inventors: Edward M. Gillis, San Jose, CA (US); Andrew L. Poutiatine, Redwood, CA (US); James A. Filice, Los Gatos, CA (US); Peter Wickman, San Francisco, CA (US); John Culwell, Los Gatos, CA (US); John S. Dinka, Fairfax, VA (US)

(73) Assignee: Durect Corporation, Cupertino, CA (US)

( * ) Notice: Subject to any disclaimer, the term of this patent is extended or adjusted under 35 U.S.C. 154(b) by 0 days.

(21) Appl. No.: 11/444,934

(22) Filed: May 31, 2006

(65) Prior Publication Data

US 2006/0224145 A1 Oct. 5, 2006

Related U.S. Application Data

(63) Continuation of application No. 10/490,331, filed as application No. PCT/US02/27856 on Aug. 29, 2002, now abandoned.

(60) Provisional application No. 60/323,406, filed on Sep. 17, 2001.

(51) Int. Cl.
*A61K 9/22* (2006.01)

(52) U.S. Cl. .................................... 604/891.1

(58) Field of Classification Search ............... 604/890.1, 604/891.1, 93.01, 131, 288, 422, 423, 424, 604/425
See application file for complete search history.

(56) References Cited

U.S. PATENT DOCUMENTS

| | | | |
|---|---|---|---|
| 3,200,585 A | 8/1965 | Climent et al. | |
| 3,938,741 A | 2/1976 | Allison | |
| 4,143,812 A | 3/1979 | Fortune | |
| 4,212,424 A | 7/1980 | Fortune | |
| 4,838,862 A * | 6/1989 | Baker et al. | 604/892.1 |
| 5,196,002 A * | 3/1993 | Hanover et al. | 604/891.1 |
| 5,217,449 A * | 6/1993 | Yuda et al. | 604/890.1 |
| 5,672,167 A | 9/1997 | Athayde et al. | |
| 5,690,952 A * | 11/1997 | Magruder et al. | 424/423 |
| 5,728,396 A | 3/1998 | Peery et al. | |
| 5,941,813 A * | 8/1999 | Sievers et al. | 600/16 |
| 5,984,209 A | 11/1999 | Weth | |
| 6,047,906 A | 4/2000 | Plager et al. | |
| 6,126,628 A | 10/2000 | Nissels | |
| 6,143,276 A | 11/2000 | Unger | |
| 6,270,483 B1 | 8/2001 | Yamada et al. | |
| 6,524,305 B1 * | 2/2003 | Peterson et al. | 604/892.1 |

FOREIGN PATENT DOCUMENTS

WO WO 97/27840 7/1997

* cited by examiner

*Primary Examiner*—Nicholas D Lucchesi
*Assistant Examiner*—Christopher D Koharski
(74) *Attorney, Agent, or Firm*—Thomas P. McCracken

(57) ABSTRACT

Implantable delivery devices (1) for accurately controlling release of an agent therefrom and for preventing release of the agent during storage, prior to use. The devices include a reservoir (3) for storing the agent, a driving means for driving the agent from the reservoir (3) and a valving and control mechanism (10) which is positively actuatable between a closed configuration and an open configuration.

26 Claims, 10 Drawing Sheets

DEVICE AND METHOD FOR ACCURATE DELIVERY OF AN ACTIVE AGENT

CROSS-REFERENCE TO RELATED APPLICATION

This application is a continuation of U.S. application Ser. No. 10/490,331, filed 29 Nov. 2004 now abandoned, which is a Rule 371 of International Application No. PCT/US02/27856, filed 29 Aug. 2002, which international application claims priority benefit of U.S. Provisional Application No. 60/323,406, filed 17 Sep. 2001.

FIELD OF INVENTION

The present invention relates generally to implantable delivery devices, and more particularly to accurately controlling the delivery of an agent from a device, as well as preventing release of an agent from a device during shelf storage.

BACKGROUND OF THE INVENTION

Controlled delivery of beneficial agents such as drugs in the medical and veterinary fields has been accomplished by a variety of methods that may employ various types of drug delivery device. A range of exemplary devices and methods are well described in "Encyclopedia of Controlled Drug Delivery" 1999, published by John Wiley & Sons Inc, edited by Edith Mathiowitz. Drug delivery devices including an implantable device, which device can be based on, for example, diffusive, erodible or convective systems, e.g., pumps, such as osmotic pumps, that may or may not be connected to a catheter, biodegradable implants, electrodiffusion systems, electroosmosis systems, vapor pressure pumps, electrolytic pumps, effervescent pumps, piezoelectric pumps, electrochemical pumps, erosion-based systems, electromechanical systems, liposomes, depots, or microspheres. Every containerized device requires an orifice of one sort or another, and such an orifice must address the particular needs of drug delivery in a certain situation, such as the need for low flow rate, steady, predictable flow rate and the need to keep the orifice closed until flow is required.

One approach for delivering a beneficial agent involves the use of implantable diffusional systems. For example, subdermal implants for contraception are descried by Philip D. Darney in Current Opinion in Obstetrics and Gynecology, 1991, 3:470-476. Norplant® requires the placement of 6 levonorgestrel-filled silastic capsules under the skin. Protection from conception for up to 5 years is achieved. The implants operate by simple diffusion, that is, the active agent diffuses through the polymeric material at a rate that is controlled by the characteristics of the active agent formulation and the polymeric material.

Another method for controlled prolonged delivery of a beneficial agent involves the use of an implantable osmotic delivery system. Osmotic delivery systems are very reliable in delivering the beneficial agent over an extended period of time. The osmotic pressure generated by an osmotic pump also produces a delivery rate of the beneficial agent into the body which is relatively constant as compared with other types of delivery systems.

In general, osmotic delivery systems operate by imbibing fluid from the outside environment and releasing corresponding amounts of the beneficial agent Osmotic delivery systems, commonly referred to as "osmotic pumps", generally include some type of a capsule having walls which selectively pass water into an interior of the capsule which contains a water-attracting agent. The absorption of water by the water-attracting agent within the capsule reservoir creates an osmotic pressure within the capsule which causes the beneficial agent to be delivered from the capsule. The water-attracting agent may be the beneficial agent delivered to the patient, however, in most cases, a separate agent is used specifically for its ability to draw water into the capsule.

When a separate osmotic agent is used, the osmotic agent may be separated from the beneficial agent within the capsule by a movable dividing member or piston. The structure of the capsule is such that the capsule does not expand when the osmotic agent takes in water. As the osmotic agent expands, it causes the movable dividing member or piston to move, which in turn causes the beneficial agent to be discharged through an orifice at the same volumetric rate that water enters the osmotic agent by osmosis.

Another method for controlled prolonged delivery of a beneficial agent involves the use of an implantable chemical or electrochemical delivery system. A controlled delivery device for holding and administering a biologically active agent includes a housing which encloses a displacing member, a chemical or electrochemical cell that generates pressure, and may include activation and control circuitry. The electrochemical or chemical cell generates gas within the housing, forcing the displacing member against the beneficial agents contained within the housing and forcing the beneficial agents through an outlet port and into the environment of use at a predetermined rate.

The orifice in any of the above devices controls the interaction of the beneficial agent with the external fluid environment. The orifice serves the important function of isolating the beneficial agent from the external fluid environment, since any contamination of the beneficial agent by external fluids may adversely affect the utility of the beneficial agent. For example, the inward flux of materials of the external fluid environment due to diffusion or osmosis may contaminate the interior of the capsule, destabilizing, diluting, or otherwise altering the beneficial agent formulation. Another important function of the orifice is to control or limit diffusional flow of the beneficial agent through the orifice into the external fluid environment.

In known delivery devices, these functions have typically been performed by flow moderators. A flow moderator may consist of a tubular passage having a particular cross sectional area and length. The cross sectional area and length of the flow moderator is chosen such that the average linear velocity of the exiting beneficial agent is higher than that of the linear inward flux of materials in the external environment due to diffusion or osmosis, thereby attenuating or moderating back diffusion and its deleterious effects of contaminating the interior of the osmotic or diffusion pump.

In addition, the dimensions of the flow moderator may be chosen such that the diffusive flux of the beneficial agent out of the orifice is small in comparison to the convective flux. One problem with flow moderators, however, is that the passage may become clogged or obstructed with particles suspended in the beneficial agent or in fluid from the external environment. Such clogging may be reduced or eliminated by increasing the diameter of the passage to 5 mil or more, for example. However, this increase results in a greater rate of diffusion of the beneficial agent out of the pump. A corresponding increase also occurs in the back diffusion of the external fluid into the pump which may contaminate the beneficial agent and adversely affect the desired delivery rate of the beneficial agent. Tolerances during fabrication also frequently dictate that the orifice diameter be greater than about 5 mils.

Systems with a long straight flow moderator are also impractical for implantation applications because they increase the size of the implant significantly making the system difficult to implant.

Leakage of the beneficial agent from the pump or device, prior to implanting the same, may occur due to pressure changes in the reservoir containing the beneficial agent caused by changes in temperature of the environment that the pump is being stored in. Loss of beneficial agent to the environment through evaporation is another common occurrence to varying degrees during the storage or shelf life of various implantable pumps.

Another problem associated with pressure driven implantable drug delivery devices is known as the burst effect, wherein, due to thermal expansion of a drug or other beneficial agent upon removing the implantable device from a room temperature, shelf environment and implanting it into an environment at body temperature, an initial volume or bolus of the drug or beneficial agent is delivered from the device which is often much larger than a predetermined measured dose called for. This phenomenon can be a critical problem, causing severe damage or even death to the patient in the worst scenarios.

Current flow modulators also cause separation of beneficial agents which contain suspensions of bioactive macromolecules (proteins, genes, etc.). When such suspensions pass along a restriction in current flow modulators, the suspension separates and the delivery concentration of bioactive macromolecules varies.

Additionally, if a drug formulation is allowed to sit in a delivery outlet channel during storage, then precipitation of solutes out of solution (due to evaporation and surface effects) may cause the delivery outlet channel to become blocked with precipitated solute.

The above problems are particularly acute when the drug to be delivered is highly potent, when the volume to be delivered is small, and when delivery is done aver a prolonged period of time.

Thus, there is a need for methods and devices that solve the problems of keeping the system closed until needed, controlling drug burst due to differential thermal expansion of the drug and the container, reducing precipitation of drug causing blockage of the outflow channel, and providing a uniform, even and predictable flow of drug out of the drug delivery device. The current invention fulfills these needs.

SUMMARY OF THE INVENTION

The invention is a manually or positively actuated valve on the exit orifice of the reservoir of an implantable pumping device. The valve allows for the system to be closed during its shelf life and thus prevents the exit of fluid out of the reservoir of the system during storage. Prior to operation of the system, the valve is positively actuated (this can be a manual actuation performed by the user through pushing, pulling, or turning a component of the valve) by the user. Examples of valve designs which incorporate each of the three mechanisms are disclosed in the attached figures.

The valve designs must contain several important features. The first feature is that the valve must allow room for thermal expansion of the contents of the pump after it has been actuated. This is important so as to control the release of drug substance which is contained in the pump due to the increase of the temperature of the pump contents from room temperature to body temperature. The next feature which is important to the valve is that it be positively or manually actuated so as to allow for a fully patent outflow track or exit orifice once it is actuated. This is important so as to allow for even flow of the contents from the pump during operation. Systems which are spring loaded or which use the buildup of pressure in the system as a means to actuate the valve have been shown to provide erratic pumping performance due to the buildup and relieving of pressure in the pump reservoir during operation. A fully patent orifice which is yielded from positive manual actuation of the valve does not allow for this buildup and release of pressure on the reservoir and the subsequent erratic release of drug formulation which results. The next feature the valve needs to have is the ability to be produced of substantially biocompatible materials if used in an implant application. In addition, the valve needs to be able to withstand the pressure buildup which occurs in the reservoir of the closed system during temperature and atmospheric pressure cycling of the system in storage.

These and other objects, advantages, and features of the invention will become apparent to those persons skilled in the art upon reading the details of the devices and methods as more fully described below.

BRIEF DESCRIPTION OF THE DRAWINGS

The present invention will be more readily understood upon reading the following detailed description in conjunction with the drawings, a brief description of which follows.

DETAILED DESCRIPTION OF PREFERRED EMBODIMENTS

Figure 1:
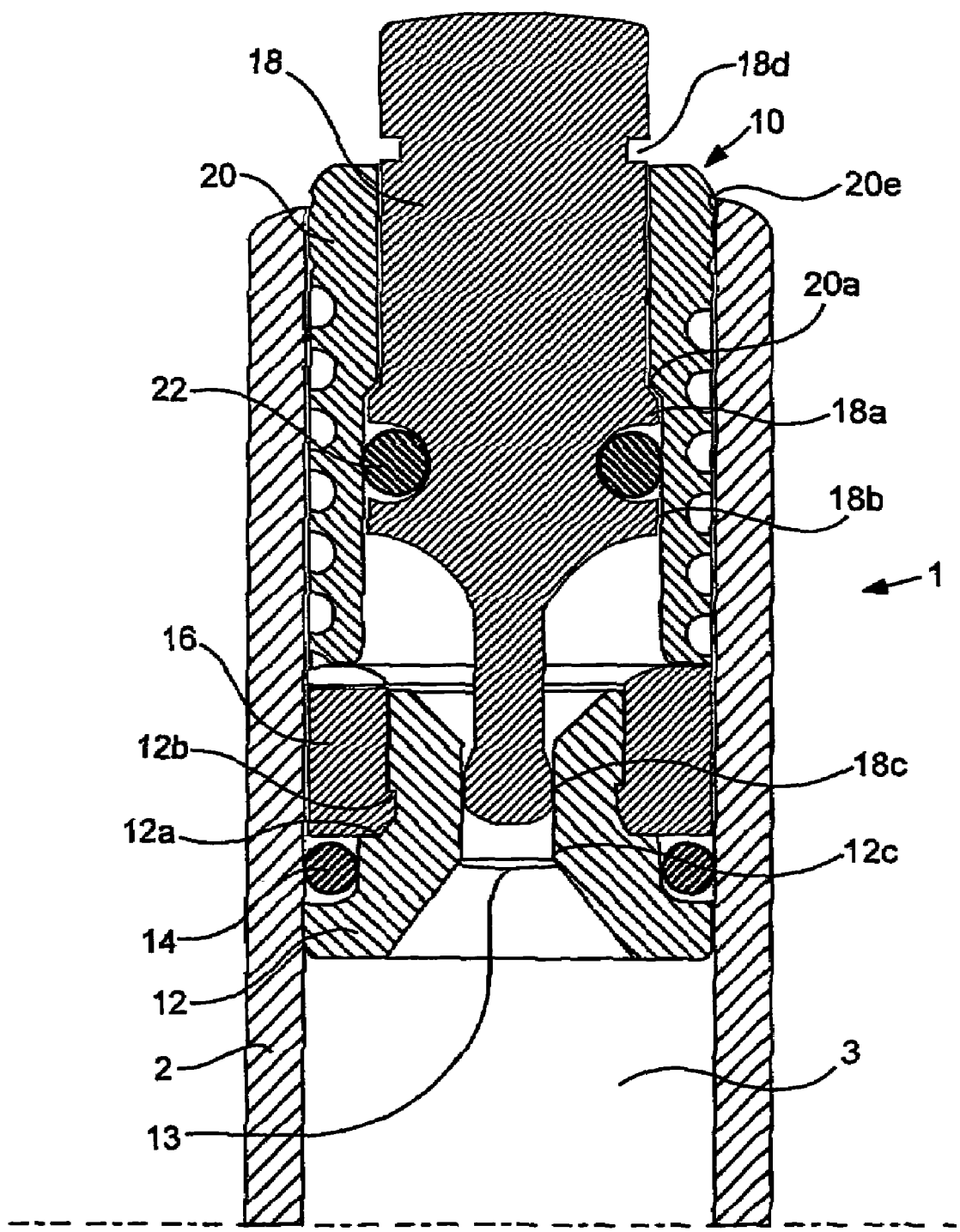
FIG. 1 illustrates a portion of a delivery device employing a flow control arrangement according to the present invention in a position at which flow is prevented.

Before the present flow control arrangements, delivery devices and methods of controlling flow are described, it is to be understood that this invention is not limited to particular mechanisms described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "e" include plural referents unless the context clearly dictates otherwise. Thus, for example, reference to "a ring" or "an O-ring" includes a plurality of such rings or O-rings and reference to "the flow path" includes reference to one or more flow paths and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DEFINITIONS

The term "agent" includes water, an electrolyte, any physiologically or pharmacologically active substance or substances, or combinations thereof. An agent may further optionally include other pharmaceutically acceptable carriers and/or additional ingredients such as antioxidants, stabilizing agents, permeation enhancers, etc.

The term "reservoir" refers to a chamber or containment space within a delivery device for storing an agent to be delivered from the delivery device.

The term "flow path" refers to the pathway taken by an agent as it is dispensed from a reservoir of a delivery device to the outside of the delivery device.

The present invention encompasses methods and devices for providing an implantable drug delivery device having a closed system reservoir that substantially prevents leakage or evaporation of the contents of the reservoir during the shelf life of the device. The present invention also accommodates for thermal expansion of the drug or beneficial agent as well as any driving media contained within the device which is experienced upon a change of temperature of the environment in which the device resides. One example of such change in temperature is that experienced when a device is moved from a "shelf" environment of approximately room temperature, to a body temperature environment upon implantation of the device into a human or animal patient. However, other significant temperature changes can occur, even during storage of a device (i.e., during its shelf life). Such accommodation prevents deleterious burst effects upon implantation of a device according to the present invention.

Referring to FIG. 1, an example of a drag delivery device 1 exhibiting all of the above described characteristics is shown. The device includes a housing or pump body 2 that houses a reservoir 3 for holding a drug or beneficial agent to be delivered from the device 1. The driving force for driving drug out of the reservoir 3 and the device and to a delivery site may be osmosis, diffusion, electrodiffusion, electroosmosis, electrochemical for example, although the present invention is not limited only to implantable devices driven by these modalities, but may also include actively driven devices (e.g., motor-driven) for example, or any other membrane modulated device which delivers drug to a treatment site.

Housing or pump body 2 may be made of titanium for example, or other relatively rigid and biocompatible structural materials such as platinum alloys, tungsten, gold, medical grade stainless steel or other inert metals or alloys, plastics such as polyethylenes, nylons, PETS etc. Housing 2 surrounds a reservoir 3 which is provided for containing a drug or beneficial agent to be delivered from device 1 to an environment of use. At a lower end of device 1 (not shown), housing 2 further contains a piston or other driver, which separates the drug and reservoir 3 from another chamber that houses a driving mechanism for the device. As noted, the driving mechanism may be an osmotic pump arrangement, diffusion pump arrangement chemical or electrochemical pump arrangement, or other modality. Examples of some of these modalities can be found in U.S. Pat. Nos. 5,169,383; 5,951,538; 5,567,287; 4,886,514; 5,593,552; 5,538,605; 5,454,922; 5,707,499; and 5,855,761, for example, each of which is incorporated herein in its entirety, by reference thereto.

At the upper end of the device a valving and control mechanism 10 is fixed at least partially within housing 2 to form a closed system reservoir 3 for storage of the device 1 and for controlled delivery of drug/beneficial agent upon actuation of the valving and control mechanism 10. A bottom ring assembly is secured adjacent reservoir 3 with a bottom end of the bottom ring assembly contacting the drug/beneficial agent contained within reservoir 3. The bottom ring assembly in this example includes a valve seat member 12 fitted within a bottom ring 16 and at least one O-ring 14 forming a seal between the valve seat member 12 and inner walls of housing 2. Valve member 12 may be formed of ultra high molecular weight polyethylene (UHMWPE), or polyethylene, or other biocompatible polymer exhibiting sufficient strength and low creep characteristics to serve as a valve seat with plunger 18 acting there against, e.g. (but not limited to): flouroelastomer (Viton™), high or low density polyethylene, linear low density polyethylene etc.

The bottom ring assembly is press fit (e.g., with about 150 lbf in this example) or otherwise securely fixed within housing 2 so that the bottom of valve seat member 12 contacts the contents of reservoir 3. As the bottom ring assembly is positioned against the reservoir 3 any air existing therebetween is drawn out by a removable vacuum line (not shown) inserted through valve neck 12c, and the valve seat member is positioned so that a meniscus 13 formed by the top of the drug/beneficial agent forms at the top of bottom cone 12d formed in the valve seat member 12. Bottom cone 12d acts to focus or funnel the drug/beneficial agent into the valve neck 12 of valve seat member 12.

Bottom ring 16 is locked within shoulders 12a,12b of valve seat member 12 to provide additional stability to the placement of the valve seat member 2 and to provide integrity of the bottom ring assembly during insertion into housing 2. Bottom ring 16 may be formed of titanium, for example, or other relatively rigid and biocompatible structural materials such as platinum alloys, tungsten, gold, medical grade stainless steel or other inert metals or alloys, plastics such as polyethylenes, nylons, PETS etc. and provides a superior anchoring function due to the larger area of surface contact between bottom ring 16 and the inner walls of housing 2 (relative to the area of surface contact between valve seat member 12 and housing 2) and/or by making bottom ring 16 to have a slightly larger outside diameter than the largest outside diameter of valve member 12 so as to develop relative greater compressive forces when inserted in housing 2. Interlocking with shoulders 12a,12b prevents movement of the valve seat member either upwardly or downwardly with respect to housing 2, thereby securely situating it in contact with the drug or beneficial agent in reservoir 3.

O-ring(s) 14 provide additional assurance that leakage/evaporation of drug/beneficial agent does not occur between the valve seat member 12/bottom ring assembly and the housing 2. Bottom O-ring(s) 14 may be made of VITON™ or any other biocompatible rubbers or polymers suitable for performing the sealing function indicated, e.g. (but not limited to): silicone rubber, butyl rubber, C-flex™, flouroelastomer, high or low density polyethylene, linear low density polyethylene etc.

A top ring assembly is secured in the open end of housing 2 with a bottom end of the top ring assembly abutting the top end of the bottom ring assembly to complete the valving and control mechanism 10. The top ring assembly in this example includes a plunger 18, fitted within a top ring 20 and at least one O-ring 22 forming a seal therebetween. As plunger 18 is designed to slide within top ring 20, O-ring 22 may be situated between a pair of shoulders 18a,18b to maintain O-ring 22 in the same position relative to plunger 18 as plunger 18 slides. Shoulders 18a,18b maintain the relative position of O-ring(s) 22 while permitting O-ring(s) 22 to slide or roll along the inner walls of top ring 20, all the while maintaining the seal between plunger 18 and top ring 20.

Shoulder 18a also abuts against shoulder 20a of top ring 20 during insertion of the top ring assembly into device 1. Plunger 18 and top ring 20 are dimensioned so that upon fitting into housing 2, the shoulder abutment 20a,18a ensures that the plunger seal 18c of plunger 18 is properly placed within the valve neck 12c of valve 12 where it seats with the valve, when the bottom end of top plug 20 abuts against the top end of bottom plug 16. The top ring assembly is securely positioned within housing 2, by press-fitting (e.g., with about 50 lbf) or by other fluid and vapor tight method of securing, such that reservoir 3 becomes a closed system for shelf storage. By press fitting the components as described, the assembly 10 can withstand back pressures (i.e, pressures provide by the drug driven by the pumping system) of up to about 5000 psi. Since most pumping systems are designed to back out at about 1000 psi this arrangement provides more than an adequate margin of safety. The seal formed between plunger seal 18c and valve neck 12c forms a fluid and vapor tight seal, while O-ring(s) 22 provide additional assurance that no leakage/evaporation of drug/beneficial agent leaks or evaporates between plunger 18 and top ring 20 to the environment. Top ring 20 and plunger 18 may be made of titanium, for example, or other relatively rigid and biocompatible structural material such as those described previously. Top O-ring(s) 22 may be made of VITON™ or any other biocompatible materials described above for use in making O-ring 14.

A location groove 18d is provided in plunger 18 to ensure proper placement of plunger 18 relative to top ring 20, which ultimately ensures proper positioning and sealing of the plunger seal 18c of plunger in valve neck 12c upon assembly. Since plunger 18 is slidable with regard to top ring 20, it is possible that plunger 18 could be inadvertently depressed, or slid downwardly, at least partially relative to top ring 20 during assembly. This could possibly result in distending plunger seal 18c below valve neck 12c so that a proper seal for shelf storage would not be formed. Location groove 18d is formed at a location along plunger 18 which ensures that, as long as location groove 18d is visible, it is assured that the plunger 18 is located with shoulder 18a abutted against shoulder 20a, or plunger 18 is at least high enough relative to top ring 20 so that plunger seal 18c will seat with valve seat 12 in the valve neck 12c.

By assembling both bottom and top ring portions as described above, valving and control mechanism 10 converts reservoir 3 to a closed system reservoir, thereby sealing the contents of reservoir 3 (drug/beneficial agent) for shelf storage of device 1 and preventing leakage or evaporation of the drug/beneficial agent from device 1 during storage and as long as valving and control mechanism 10 is maintained in the configuration shown in FIG. 1.

Figure 2:
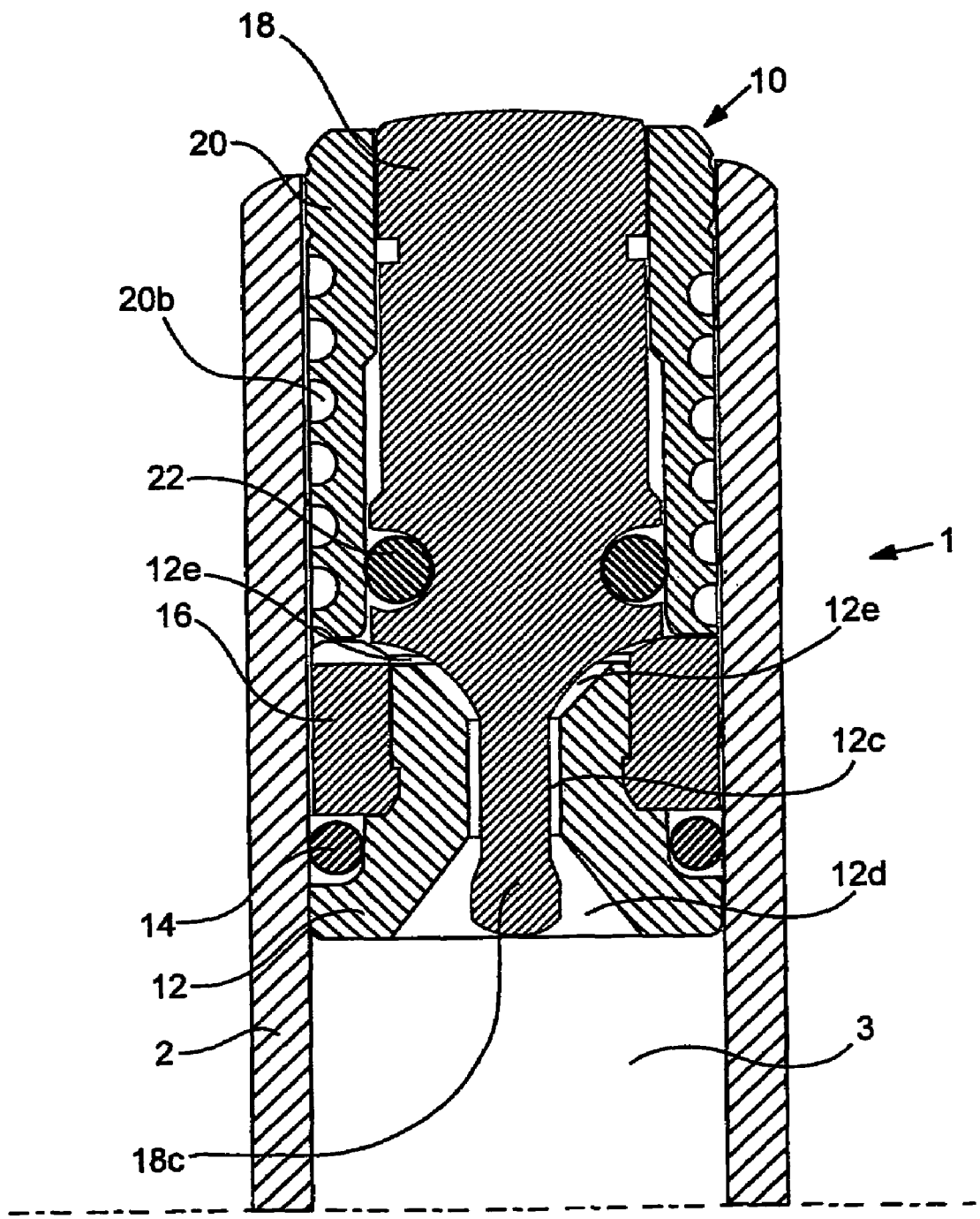
FIG. 2 illustrates the delivery device as in FIG. 1, but with the flow control arrangement positioned to allow flow from the delivery device.

When it comes time to implant device 1 or otherwise place it in an environment of use, valving and control mechanism is actuated to a use position as shown in FIG. 2, thereby opening reservoir 3 to a flow path that leads out of device 1 for delivery of drug/beneficial agent to the environment of use. In the example of FIGS. 1 and 2, plunger 18 is depressed relative to housing 2 to a position where the top of plunger 18 is substantially flush with the top end of top ring 20. Actuation/depression of plunger 18 requires about 3-4 lbf, for example, and once depressed, top O-ring 22 maintains the plunger in the depressed position against forces of up to about 0.5 lbf. This actuation forces plunger seal 18c out of valve neck 12c and into the volume defined by bottom cone 12d, thereby breaking the seal formed between plunger seal 18c and the valve seat (i.e., valve neck 12c) thereby opening a flow path through the valve seat member 12 between valve neck 12c and plunger 18. This flow path further connects with a space defined between the plunger 18 and top cone 12e formed in valve seat member, which in turn flows into channel 12e that connects with top ring flow path 20b formed in top ring 20 and bordered by the inner walls of housing 2. The flow pathway thus defined forms a widely patent or open exit channel which allows the uniform flow of drug/beneficial agent from the reservoir 3 to the environment of use during the operation of the pumping system as it provides a driving force to the reservoir 3.

When describing the exit channel as "widely patent" it is meant that the channel is clearly open and unobstructed with a continuous size sufficient to allow clear, even and unobstructed flow of a fluid therethrough. This is an important advantage of the present system over certain other designs that employ a build-up of pressure within the device to force open a valve (such as a spring-loaded valve). The problem with such pressure-opened designs is that they become briefly open when the pressure inside has built up to a sufficient degree, but once the pressure is released upon opening, the valve tends to shut again, and although theoretical calculations would indicate that a constant pressure would be reached to produce an even flow, this has not proved the case experimentally, such pressure release designs produce an uneven and/or intermittent flow that may be highly undesired when delivering a potent drug.

In the example shown, top ring flow path is formed as a spiral pathway, which provides a relatively larger volume capacity than a straight flow pathway would, given the same cross-sectional dimensions of the pathways. The flow pathways described above (including top ring flow path 20b and the pathways connecting it to the drug/beneficial agent) provide a thermal expansion space or capacity for the drug/beneficial agent to flow into after actuation of the valving and flow control mechanism (FIG. 2) to prevent a burst effect upon implantation of device 1 into an organism or other environment of use having a significantly higher temperature that would cause the volume of the drug/beneficial agent to expand and thus drive an amount of drug/beneficial agent from the reservoir prior to any pumping action by the pumping mechanism For example, a drug formulation in a device as shown might expand by about 2 microliters in a device 1 with a titanium housing 2 after stabilization of the temperature of the device after having been moved from a room temperature environment to a human body temperature environment. In such a case, the flow pathways would be designed to have a volume of about 3 microliters so as to have an extra margin of safety to ensure that a burst of drug would not be initially delivered to the patient upon implantation. Of course, the volumes described are only an example, and the actual volume of the flow pathways for preventing burst will vary depending upon the total volume of the drug in the reservoir, the cross sectional area(s) of the flow pathways, the change in temperature from the first to the second environment, etc. Generally, however, the volume of the flow pathways will be designed such that, upon thermal expansion of the drug/beneficial agent in the environment of use, the drug/beneficial agent will extend about two thirds of the way along the length of the top ring flow path 20b.

Figure 3:
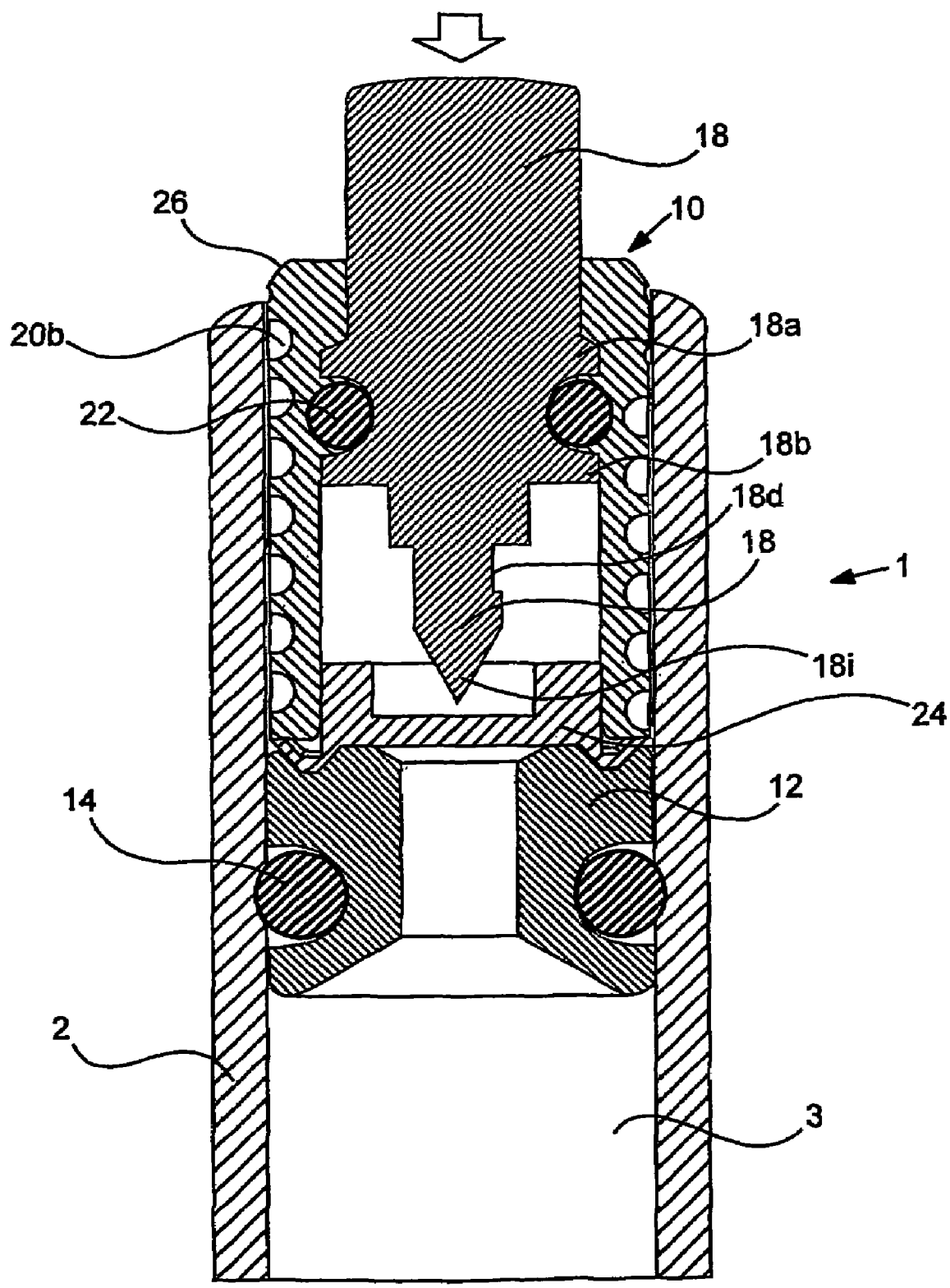
FIG. 3 illustrates a portion of a delivery device employing another flow control arrangement according to the present invention in a position at which flow is prevented.

FIG. 3 is a partial view of a drug delivery device 1 which employs another example of a valving and flow control mechanism according to the present invention. Components that are the same or substantially similar in design and function to the counterparts described in the example of FIGS. 1 and 2 are not described here. In this example, valve seat member 12 may be formed of titanium or other similar rigid, biocompatible material, since it does not function to form a seal with plunger 18 in the storage position shown in FIG. 3, but must form a press fit with the inner walls of housing 2 that is substantially equivalent of that provided by both valve seat member 12 and bottom ring 16 in the example shown in FIGS. 1 and 2.

A septum or puncturable disk 24 overlays valve seat member 12 in a conforming manner and is sandwiched between valve seat member and top ring 20 which is press fit into abutment with septum 24, at which time septum 24 effectively seals reservoir 3 forming a closed system suitable for storage without leakage/evaporation of the drug/beneficial agent contained within reservoir 3. Septum or puncturable disk 24 may be made of silicone rubber, flouroelastomer, polyethylene, PET, or other biocompatible rubber, polymer or thin frangible metal that may be readily punctured.

The top ring assembly is secured in the open end of housing 2 similarly to that described above with the example of FIG. 1, with a bottom end of the top ring assembly abutting the septum and sealing it between the top ring 20 and valve seat member 12. The top ring assembly in this example includes a plunger 18, fitted within a top ring 20 and at least one O-ring 22 forming a seal therebetween. The plunger 18 in this example, does not form a seal with the valve seat member 12, as that function is provided by the septum 24. Although not shown, a location groove 18d may also be provided in plunger 18 of this example, to provide the same function as described above with respect to the example of FIGS. 1 and 2.

Actuation of the valving and control mechanism 10 opens reservoir 3 to a flow path that leads out of device 1 for delivery of drug/beneficial agent to the environment of use. Actuation is performed by manually or otherwise positively depressing plunger 18 relative to housing 2 to a position where the top of plunger 18 is substantially flush with the top end of top ring 20. Actuation/depression of plunger 18 drives a sharp end 18i of plunger 18 through septum 24, thereby providing an opening through septum 24 and breaking the seal of the reservoir 3. A notch, groove, hollow, or other bypass feature 18d is provided above the point 18i in a location that traverses the punctured septum 24 when plunger 18 is in the depressed position, thereby providing a more patent or open flow path for the drug/beneficial agent between septum 24 and plunger 18. The flow path continues on out to top ring flow path 20b similarly to that described above.

Figure 4:
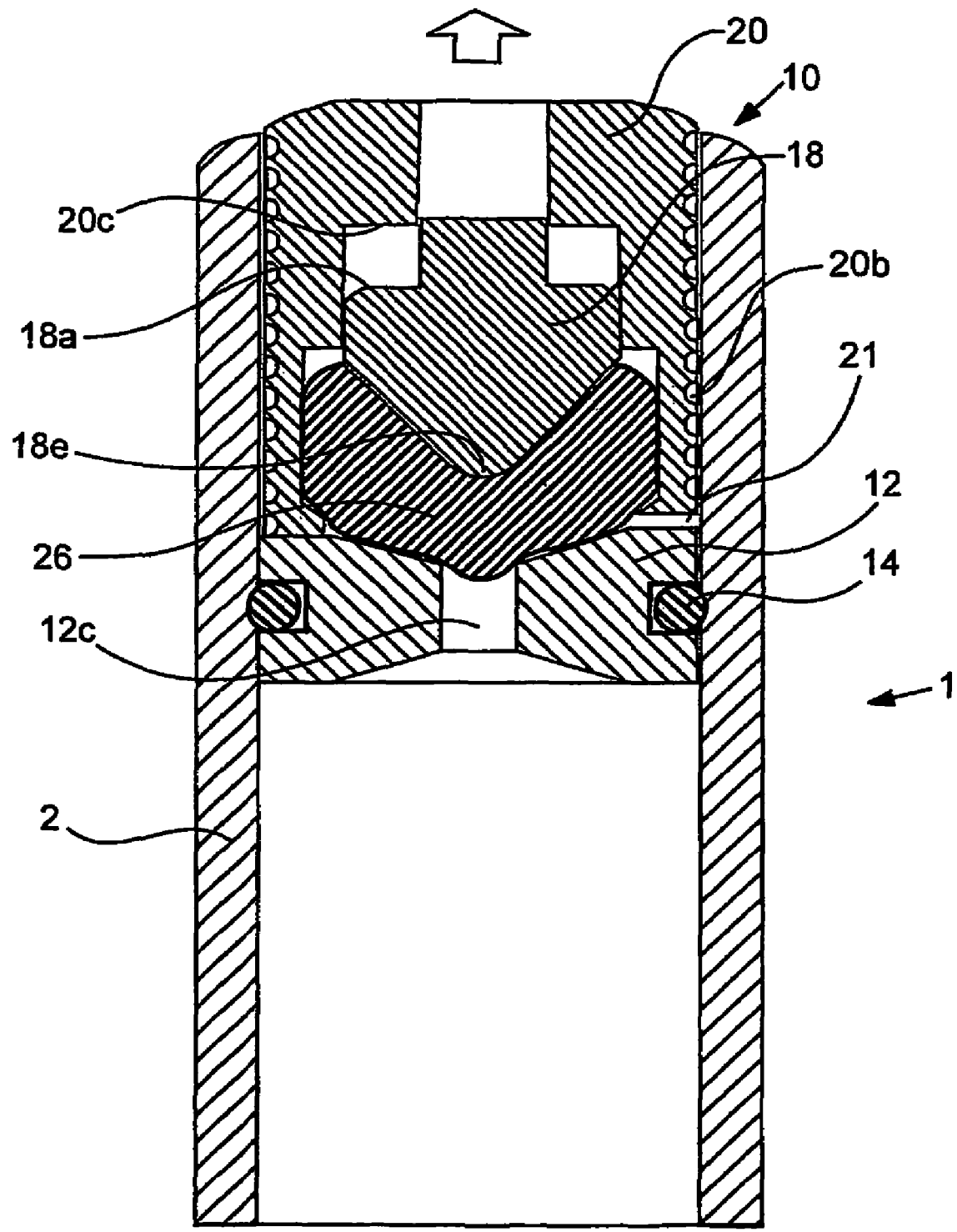
FIG. 4 illustrates a portion of a delivery device employing still another flow control arrangement according to the present invention in a position at which flow is prevented.

Turning to FIG. 4, a portion of a drug delivery device 1 is shown which employs a pull valve or a type of pulling action to actuate the valving and flow control mechanism 10. In this example, valve seat member 12 is similar to that in FIG. 3 in that it may be made of titanium or other rigid biocompatible material and serves the functions of both the valve seat member and bottom ring of FIG. 1. An O-ring 14 is provided to prevent leakage/evaporation of drug/beneficial agent between valve seat member 12 and the inner walls of housing 2. An elastomer valve seal 26 (made from suitable materials e.g., but not limited to: flouroelastomer (VITON™), high or low density polyethylene, linear low density polyethylene etc) overlies the top surface of valve seal member 12 in conforming fashion to seal off reservoir 3, thereby making it a closed system for storage. A flow path 21 connecting valve neck 12c with top ring flow path 20b can be clearly seen in FIG. 4, and is sealed off from valve neck 12c in the closed position by valve seal 26.

Plunger 18 in this example may again be made of titanium or other structurally strong and rigid biocompatible material capable of exerting a force required for sealing with little or no distortion of the plunger material (eg: from about 2-5 lbf). Plunger 18 includes a blunt tip 18e which ensures a directed force fit of valve seal 16 against the flow paths and may even partially distort the valve seal 16 to assume a position partially within valve neck 12c as shown in FIG. 4.

Figure 5:
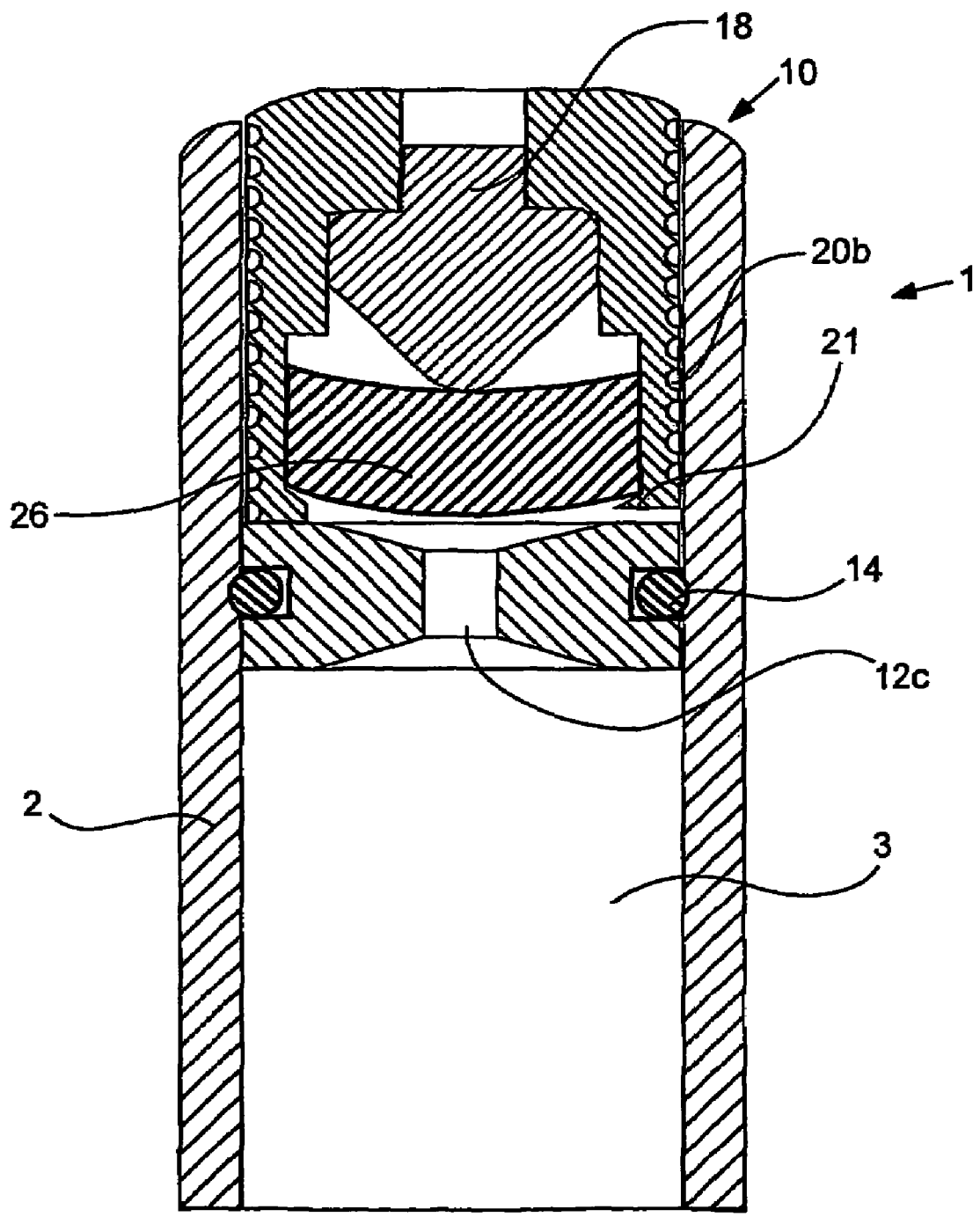
FIG. 5 illustrates the delivery device as in FIG. 4, but with the flow control arrangement positioned to allow flow from the delivery device.

Top ring 20 is similar to previous embodiments in that it contains top ring flow path 20b and in that it is press fitted or otherwise securely fixed into housing 2, However, the top portion of top ring 20 is designed to contain plunger 18 and provides stops 20c against which upper shoulders of plunger 18 abut when valving and flow control mechanism 10 is actuated, as shown in FIG. 5. Upon assembly, plunger 18 is positioned in the closed position shown in FIG. 4. It can be locked down by means of a threaded plug which, when screwed into neck of the ring (20), holds the plunger down. The plug could also be pressed into the ring (20) like a simple non-threaded plug, and held there by friction.

Actuation of mechanism 10, as opposed to earlier examples, is by pulling back on the plunger (18) to reposition plunger 18 so that shoulder 18a abuts against stops 20c, thereby opening reservoir 3 to the flow pathways 12c, 21, 20b, as shown in FIG. 5. FIGS. 4 and 5 do not show the means by which the plunger (18) is pulled out, but such a means may use the elasticity of the valve seal 26 to push the plunger out and open the valve. In such an embodiment, in the closed position, the plunger would be pushed down against the elastic resistance of the valve seal and be held in place by a suitable device such as a pin or by a simple mortise and tenon arrangement (not shown) whereby the plunger is depressed and rotated such that a tenon, projecting from the plunger 18, slides into a mortise grove, cut into the inner surface of the ring 20, to hold the plunger in place. When released, the force of the valve seal pushes the plunger back to its default (open) position. Another simple design for opening and closing the valve would be to use a screw thread between the plunger 18 and the ring 20. Alternatively a means for pulling out the plunger may be provided by a manually pullable tab or protruding portion attached to the plunger, or may be provided by a simple lock-and-key type slot in the top of the plunger that would allow the plunger to be pulled back using a very simple tool. During the pull back operation, elastomeric seal member 26, converts potential energy to kinetic energy to provide a driving force for the repositioning of plunger 18. Additionally, this example has the capability of resealing reservoir 3 if desired. Resealing can be effectuated by pressing down on the top ring 20 to return plunger 18 to the position shown in FIG. 4. Optionally, a locking mechanism (not shown) may be provided to lock the plunger in the open position shown in FIG. 5. Such a locking mechanism may be passive and may employ the screw threads mentioned earlier.

Figure 6:
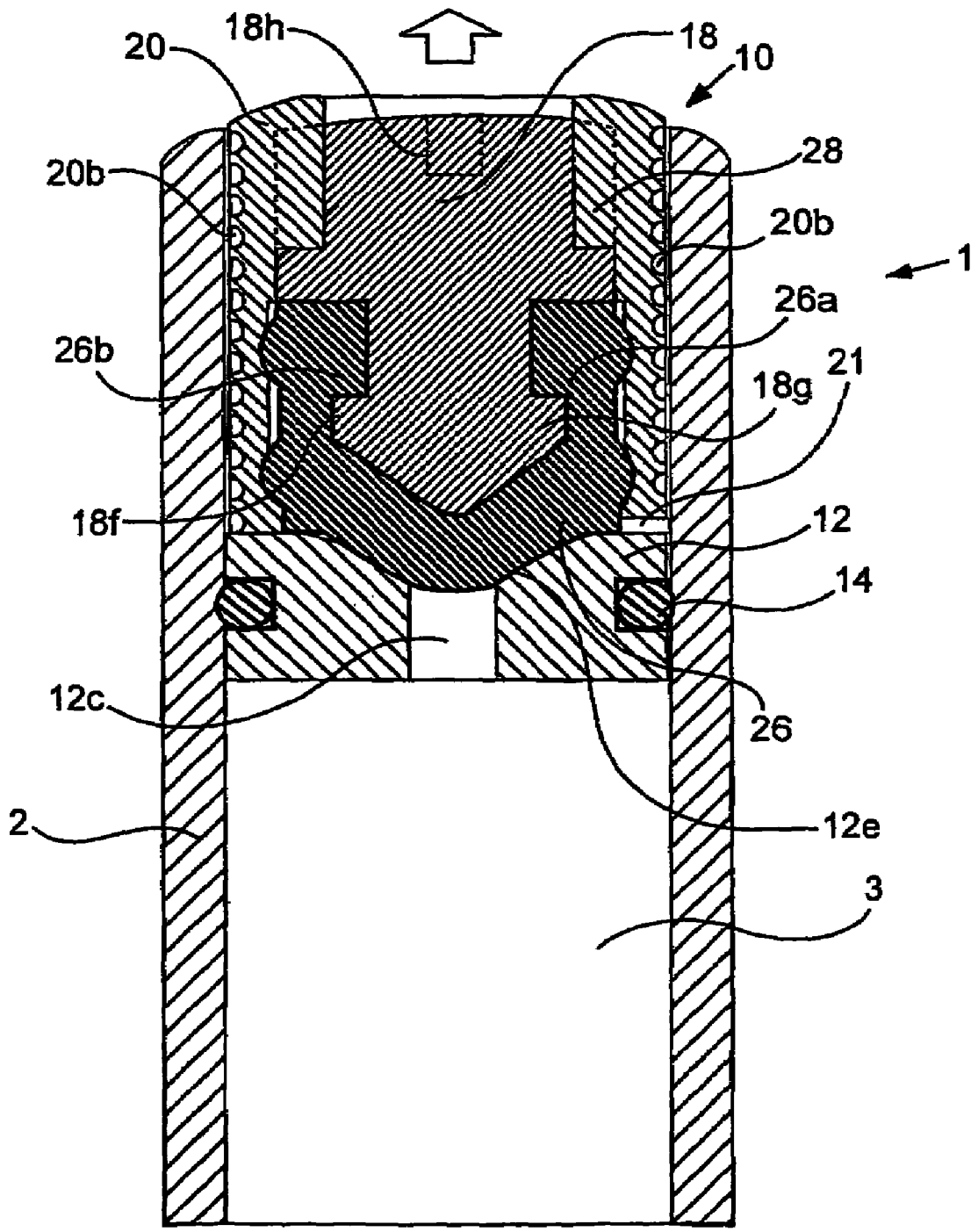
FIG. 6 illustrates a portion of a delivery device employing a variation of the flow control arrangement shown in FIGS. 4-5, in a position at which flow is prevented.

FIG. 6 shows another example of a valving and control mechanism 10 which actuates through an action of moving the plunger away from the valve sealing member 12 and elastomeric seal 26. In this instance, threads 28 are provided between plunger 18 and top ring 20, so that plunger 18 may be rotated or torqued to translate its position with regard to top ring 20. Thus to close the mechanism FIG. 6), plunger 18 is rotated in either a clockwise or counterclockwise fashion (depending upon the handedness of threads 28) to the position shown in FIG. 6 to exert a sealing pressure on elastomeric seal 26 and to force it to conform to top cone 12e of valve sealing member 12, thereby sealing off valve neck 12c and reservoir 3 and converting reservoir 3 into a closed system for storage.

Seal member 26 is interlocked with plunger 18 at shoulders 18f and 18g by shoulder portions 26a and 26b, respectively, to ensure positive direct movement of seal member with the movements of plunger 18 in both directions. A slot 18h or other tool engaging configuration (e.g., Phillips head slot, Allen receptacle, or the like) may be provided in plunger 18 for receiving a tool that may be used for rotating plunger 18. Alternatively, an extension, or other grasping conformation (not shown) may be formed to extend from plunger 18 for manual rotation thereof.

Figure 7:
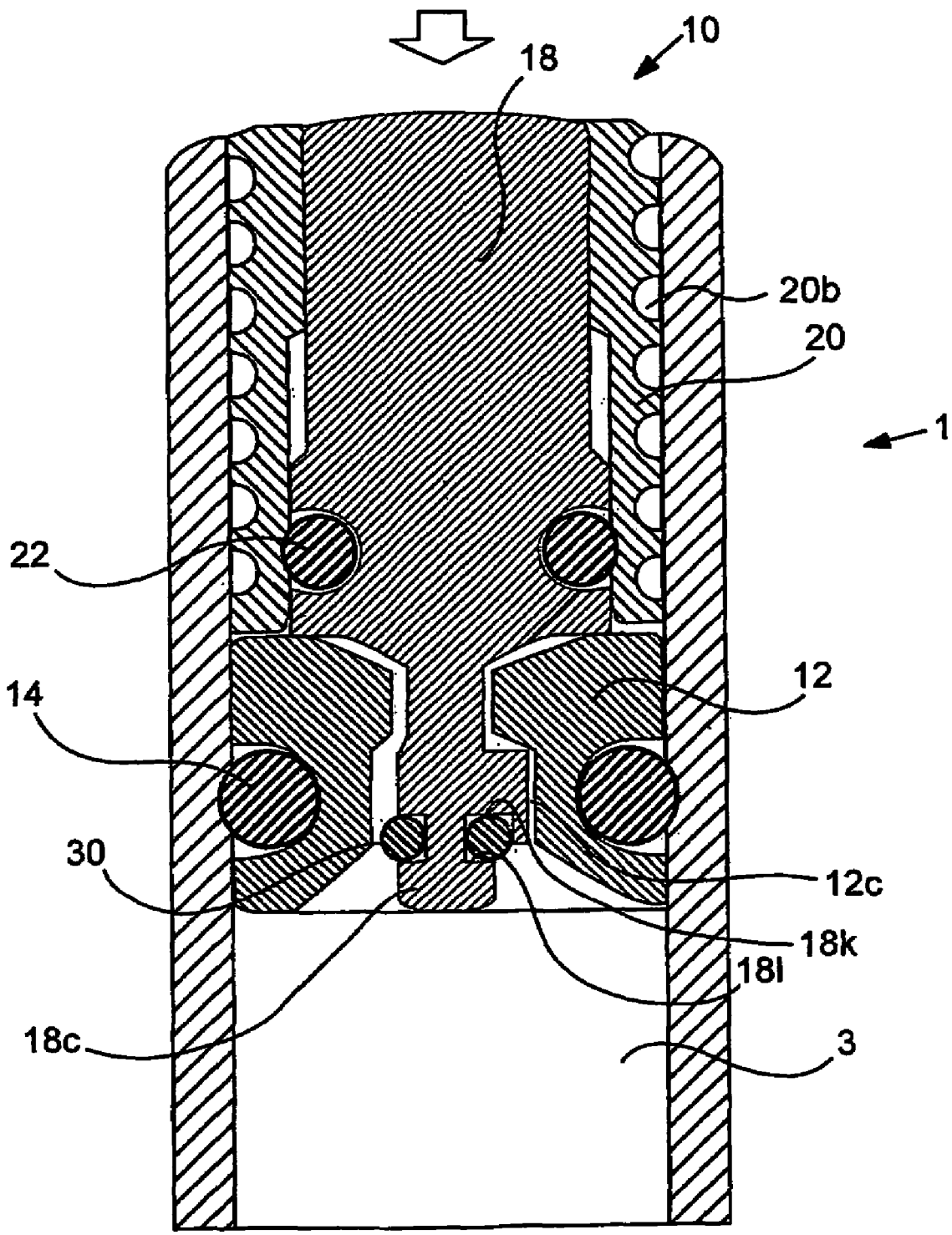
FIG. 7 illustrates a portion of a delivery device employing a variation of the flow control arrangement shown in FIG. 1, in a position at which flow is allowed.

The valving and control mechanism 10 of the device 1 partially shown in FIG. 7 functions similarly to that described above with regard to FIGS. 1 and 2, and is shown in an open or actuated position. In this example, valve seat member 12 may be formed of titanium or other similar rigid, biocompatible material, since it forms a press fit with the inner walls of housing 2 that is substantially equivalent of that provided by both valve seat member 12 and bottom ring 16 in the example shown in FIGS. 1 and 2. Since plunger 18 is also formed of titanium or other similar rigid, biocompatible material, an O-ring 30 or other sealing member is fitted on plunger seal 18c, to ensure a positive seal with valve neck 12c in the closed configuration. O-ring 30 may be situated between a pair of shoulders 18k, 18l to maintain O-ring 30 in the same position relative to plunger seal 18c as plunger seal 18c slides with respect to valve neck 12c.

Figure 8:
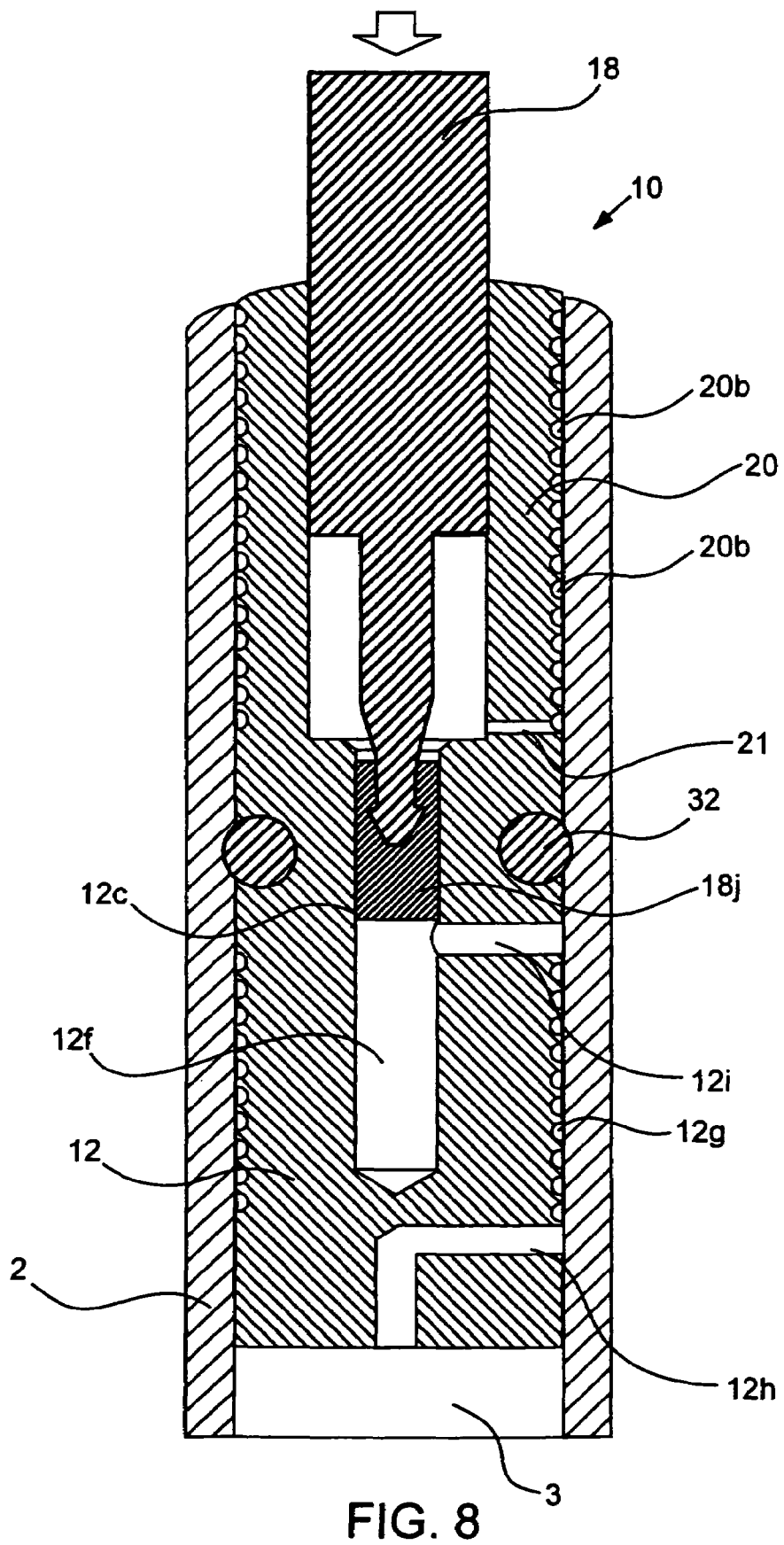
FIG. 8 illustrates a portion of a delivery device employing still another flow control arrangement according to the present invention, in a position at which flow is prevented.

FIG. 8 shows another example of a valving and flow control mechanism 10 in a drug delivery device 1 (partially shown) which is actuated by pushing or depressing plunger 18 further into the device. In this arrangement, valve seat member 12 is formed of titanium or other similar rigid and biocompatible material which can be press fit into housing 2. A bore 12f is formed in valve seat member 12 for receiving a portion of plunger 18 upon actuation of the valving and flow control mechanism 10. A flow path 12g, which in this example is a spiral flow path, but need not necessarily be (e.g. a straight flow path other configuration may be used), is provided in valve seat member 12 and formed with the inner walls of housing 2. (The advantage of the spiral path is that it is easy to machine and that it provides an overall higher volume for the drug path between the reservoir and the outside, thereby providing more stability (more "play") in the system when filing and dealing with thermal expansion). Flow path 12g connects a channel 12h leading from reservoir 3 with a channel 12i leading to bore 12f.

In the closed or storage configuration shown in FIG. 8, plunger 18 extends from the upper end of device 1 and top ring 20. Although not shown, a location groove 18d may also be provided in plunger 18 of this example, to provide the same function as described above with respect to the example of FIGS. 1 and 2. Plunger 18 may be formed of titanium or other structurally substantial and rigid biocompatible material, except the lower tip 18j is formed of polyethylene, flouroelastomer, UHMWPE or other biocompatible polymer capable of forming an acceptable seal with valve neck 12c in the closed position. As shown, lower tip 18j is mechanically interlocked with the titanium end of plunger 18 and may be molded onto the titanium in this configuration. Additionally or alternatively, lower tip 18j may be bonded to the titanium plunger end and/or further mechanically or chemically fixed as by screwing, gluing, melt bonding, or otherwise affixing it. An O-ring 32 or other sealing member is provided between valve sealing member 12 and housing 2 to assure that no leakage out of the system or evaporation of drug/beneficial agent occurs between these two components.

In the closed position lower tip 18j of plunger 18 seals with valve neck 12c to prevent flow, leakage or evaporation of drug/beneficial agent beyond the flow pathways 12h, 12g, 12i. Upon depressing plunger 18 to actuate mechanism 10 in a manner as described above, lower tip 18j is repositioned in bore 12f to a location intermediate of the flow pathways 12h and 12i. The frictional forces between lower tip 18j and bore 12f are sufficient to maintain the plunger in the open position, being capable of withstanding forces of up to about 0.5 lbf, for example. This action opens the flow pathways 12h, 12g, 12i to flow paths 21 and 20b and thus to the exterior of device 1 thereby opening reservoir 3 for delivery of drug/beneficial agent to the environment of use.

Figure 9:
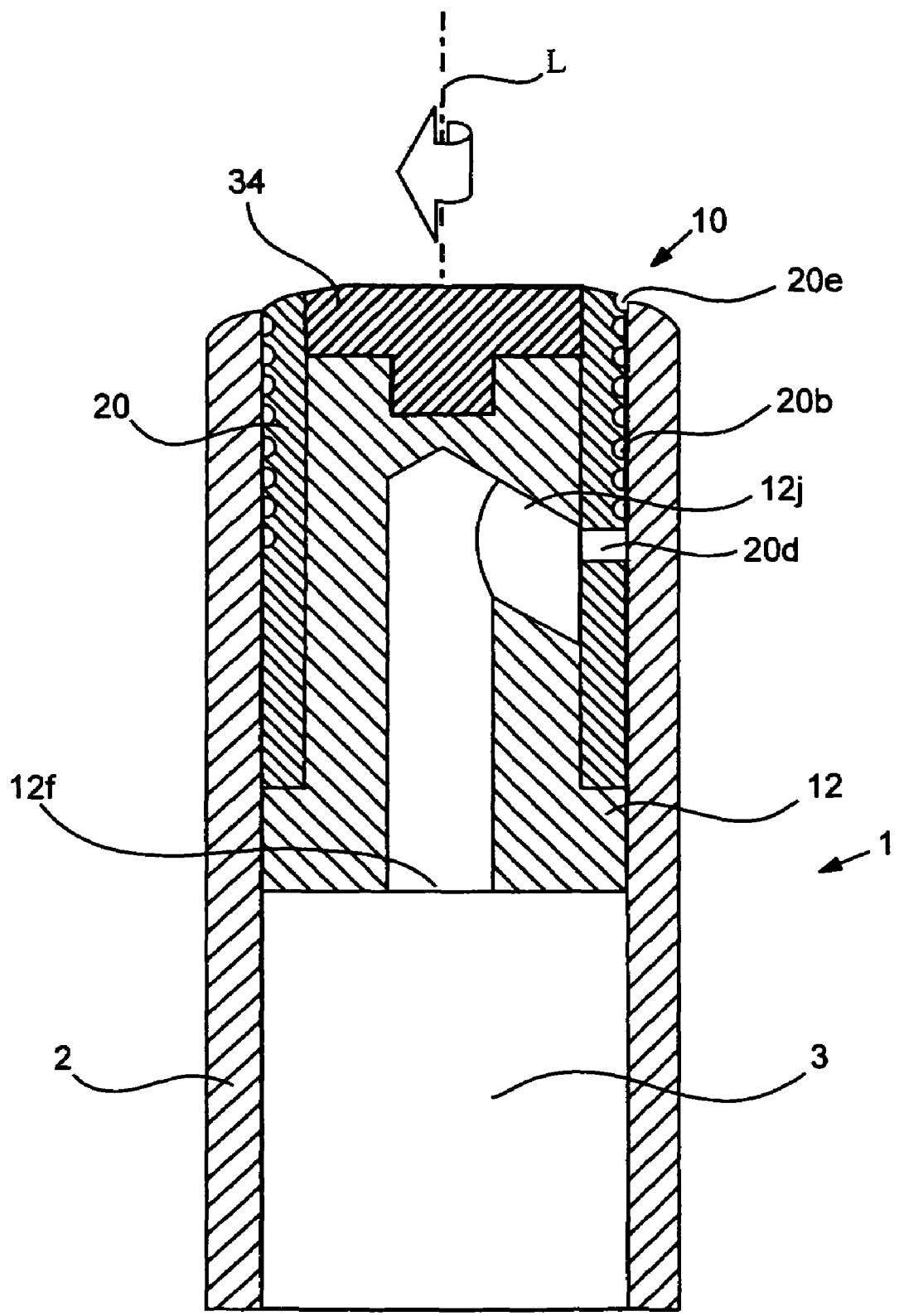
FIG. 9 illustrates a portion of a delivery device employing a flow control arrangement which is rotatable to allow or prevent flow therethrough.

FIG. 9 is another example of a valving and control mechanism 10 which is rotationally actuable in a drug delivery device 1. In this example, valve seat member 12 may be formed as a biocompatible polymer plug, out of polyethylene, UHMWPE or other biocompatible polymer having adequate structural rigidity along with a capability for forming an adequate seal with housing 2 and other titanium or structurally rigid components in the mechanism 10. Top ring 20 is press fit or otherwise securely fitted in housing 2 and abuts against valve seal member to assist in maintaining the position thereof. A top cap 34 which may be formed of titanium or other structurally rigid, biocompatible material is securely fixed to valve seat member within top ring 20. Fixation may be by gluing, heat welding or other mechanical or chemical means of fixation. Additionally, cap 34 may be mechanically interlocked with valve seat member with regard to rotational movements about the longitudinal axis L of device 1, to ensure positive rotational positioning of valve seat member 12 when cap 34 is rotated. Although not shown, cap 34 may have a slot or other tool engaging configuration (e.g., Phillips head slot, Allen receptacle, or the like) for receiving a tool that may be used for rotating cap 34, similar to that described above with regard to plunger 18 (FIG. 6). Alternatively, an extension, or other grasping conformation (not shown) may be formed to extend from plunger 18 for manual rotation thereof.

Valve seat member 12 is provided with a bore 12f that leads into the interior of the lug body of valve seat member 12 and connects reservoir 3 with a selectable flow path 12j. Selectable flow path 12j extends radially outward from bore 12f to the exterior or outer circumference of valve seat member 12. Actuation from the off or closed position to the actuated, on or "use" position shown in FIG. 9, is effected by rotation of cap 34 which in turn rots valve seat member 12 along with it, until selectable flow path 12j aligns with a flow path or hole 20d that extends through top ring 20 and connects with top ring flow path 20b that leads to the exterior of the device at 20e. In this way, an open or patent flow path 12f,12j,20d,20b,20e is established between reservoir 3 and the environment of use.

This example allows the valving and control mechanism to be shut off or sealed, even after actuating, if desired, by reverse rotation (or further rotation in the same direction) to position selectable low path 12j out of alignment with hole 20d. Optionally, the mechanism 10 may be provided with a stop (not shown) to prevent over rotation of the valve seat member 12 in the same direction of rotation once alignment has been reached during actuation. Additionally or alternatively optional (also not shown) a locking mechanism may be provided to lock the device in the actuated configuration, to prevent inadvertent total or partial closure of the flow path during use.

Figure 10:
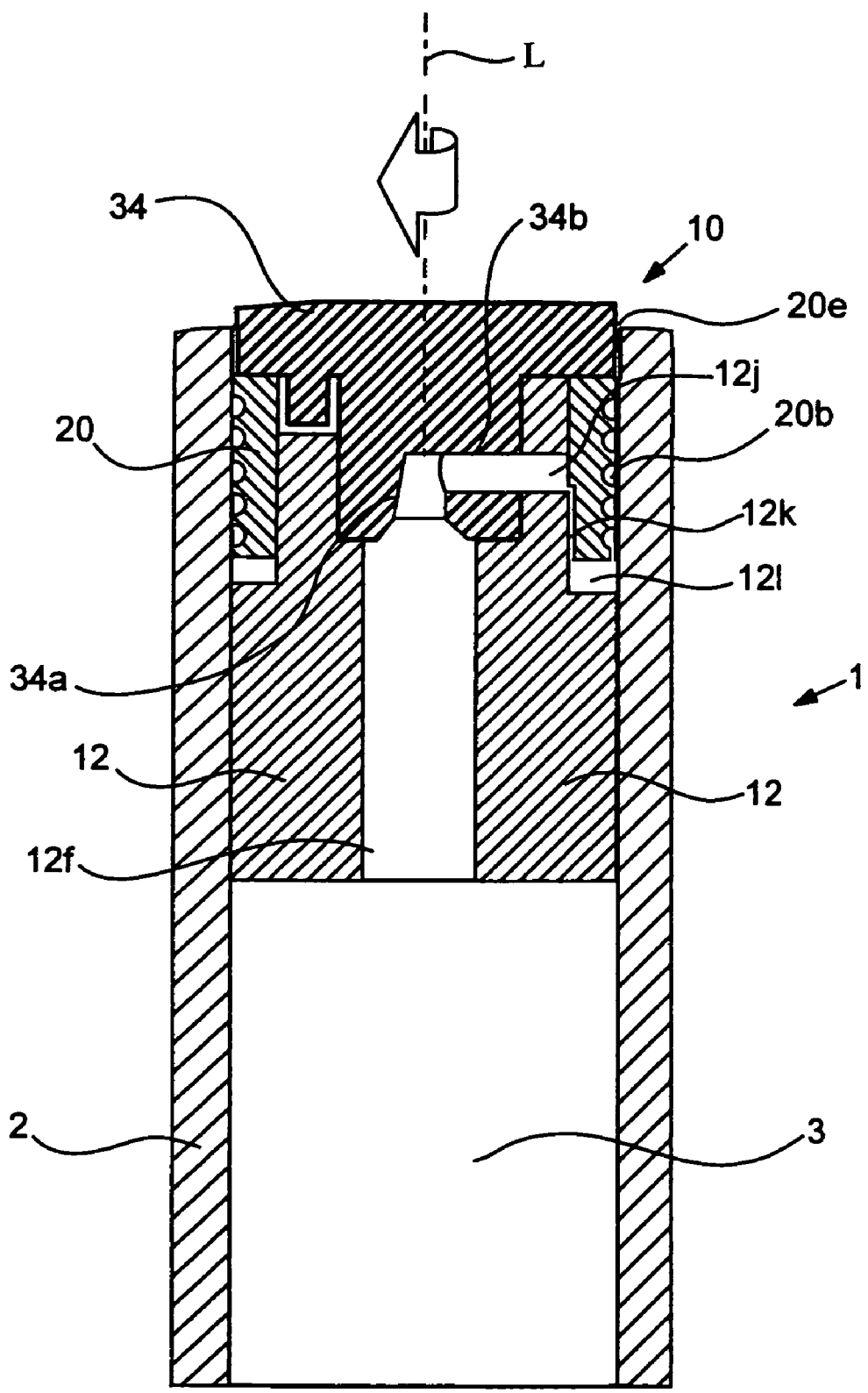
FIG. 10 illustrates a portion of a delivery device employing a variation of the flow control arrangement shown in FIG. 9 with the flow control arrangement positioned to allow flow from the delivery device.

FIG. 10 shows an example of a valving and flow control mechanism 10, in an actuated position, in a drug delivery device 1 (partially shown) which is similar to the mechanism 10 shown in FIG. 9. In this example, however, bore 12f connects with a bore 34a in top cap 34 which further has a selectable flow path 34b extending radially (and in this case substantially perpendicularly, although not necessarily so) from bore 34a. Thus, in this example, top cap 34 is selectively rotatable for alignment of selectable flow path with flow path 12j in valve seat member 12, and valve seat member 12 is fixed within housing 2 (i.e., does not rotate with the rotation of cap 34, nor does it translate). Flow path 12j is connected to a flow path 12l which leads to the exterior of valve seat member, by flow path 12k extending between the surfaces of valve seat member 12 and top ring 20. Flow path 12l connects with top rig flow path 20b that leads out of the device 1 at 20e.

Similar to the example described and shown in FIG. 9, this example allows the valving and control mechanism 10 to be shut off or sealed even after actuating, if desired, by reverse rotation (or further rotation in the same direction) of cap 34 to position selectable flow path 34b out of alignment with path or channel 12j. Optionally, the mechanism 10 may be provided with a stop (not shown) to prevent over rotation of cap 34 in the same direction of rotation once alignment has been reached during actuation. Additionally or alternatively optional (also not shown) a locking mechanism may be provided to lock the device in the actuated configuration, to prevent inadvertent total or partial closure of the flow path during use.

Additionally, cap 34 may be mechanically interlocked with valve seat member with regard to rotational movements about the longitudinal axis L of device 1, to ensure positive rotational positioning of valve seat member 12 when cap 34 is rotated. Although not shown, cap 34 may have a slot or other tool engaging configuration (e.g., Phillips head slot, Allen receptacle, or the like) for receiving a tool that may be used for rotating cap 34, similar to that described above with regard to plunger 18 (FIG. 6). Alternatively, an extension, or other grasping conformation (not shown) may be formed to extend from plunger 18 for manual rotation thereof.

While the present invention has been described with reference to the specific embodiments thereof it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the present invention That which is claimed is:

1. An implantable device for accurate delivery of an active agent, said device comprising:
   the active agent;
   a housing (2) including a reservoir (3) that contains the active agent;
   a valving and control mechanism (10) fitted at least partially within said housing (2) and fitted at least partially between the reservoir and an opening to an environment of use, wherein the valving and control mechanism comprises a valve seat member (12) peripherally sealed with respect to said reservoir and a plunger (18) adapted to slide with respect to said valve seat member (12) and said valving and control mechanism (10) is able to withstand pressure buildup in the reservoir during temperature and atmospheric pressure cycling during storage and capable of assuming an open configuration and a closed configuration, said valving and control mechanism (10) closes off said reservoir (3) when in said closed configuration, thereby preventing leakage of the active agent during storage in said device; and further wherein said valving and control mechanism (10) opens said reservoir (3) to a flow path when in said open configuration, thereby permitting controlled delivery of the active agent.

2. The device of claim 1, wherein said flow path has sufficient capacitance to accommodate thermal expansion of the agent due to a change in temperature from room temperature to a patient body temperature and upon changing said valving and control mechanism (1) from said closed configuration to said open configuration.

3. The device of claim 1, wherein said valving and control mechanism (10) is positively actuatable between said closed configuration and said open configuration.

4. The device of claim 3, therein said valving and control mechanism (10) is manually actuatable.

5. The device of claim 3, wherein said valving and control mechanism (10) is actuated from said closed configuration to said open configuration by pushing an actuation portion thereof.

6. The device of claim 3, wherein said valving and control mechanism (10) is actuated from said closed configuration to said open configuration by pulling an actuation portion thereof.

7. The device of claim 3, wherein said valving and control mechanism (10) is actuated from said closed configuration to said open configuration by rotating an actuation portion thereof.

8. The device of claim 3, wherein said valving and control mechanism (10) is further positively actuatable from said open configuration back to said closed configuration.

9. The device of claim 1, further comprising means for applying a driving force to the agent in said reservoir to drive the agent through the flow path and out of the device when said valving and control mechanism are in said open configuration.

10. The device of claim 9, wherein said means for applying a driving force is selected from the group consisting of osmotic pumps, diffusion pumps, electrodiffusion pumps, electroosmotic pumps, and electrochemical pumps.

11. The device of claim 9, wherein said means for applying a driving force comprises an actively driven device.

12. The device of claim 9, further comprising a driver separating said means for applying a driving force from the agent.

13. The device of claim 12, wherein said driver comprises a piston.

14. The device of claim 1, wherein said valve seat member has an opening therethrough including a valve neck (12c) adapted to seat with a portion (18c) of said plunger (18) when said valving and control mechanism is positioned in said closed configuration, and wherein upon sliding said plunger to push said portion (18c) out of said valve neck, said valving and control mechanism (10) is in said open configuration and said reservoir is opened to the flow path via said valve neck (12c).

15. The device of claim 14, wherein said valve seat member (12) is contained within a lower ring (16) abutting said housing (2), said device further comprising an upper ring (20) abutting said lower ring (16), said plunger (18) being slidably positioned within said upper ring (20) and said flow path extending between said housing (2) and said upper ring (20).

16. The device of claim 15, wherein said flow path spirals around said upper ring (20).

17. The device of claim 1, wherein said valving and control mechanism (10) comprises a valve seat member (12) peripherally sealed with respect to said reservoir (3) and having a passageway extending therethrough for connecting said reservoir (3) with the flow pathway; a septum (24) overlaying said passageway and sealing off the reservoir (3) when said device is in said closed configuration; and a plunger (18) adapted to slide with respect to said valve seat member (12) and to puncture said septum (24) upon pushing said plunger to pierce said septum (24) wherein said valving and control mechanism (10) assumes the open configuration and the reservoir (3) is thereby opened to the flow pathway.

18. The device of claim 17, further comprising an upper ring (20) fitted within said housing (2), said plunger (18) being slidably positioned within said upper ring (20) and said flow path extending between said housing (2) and said upper ring (20).

19. The device of claim 18, wherein said flow path spirals around said upper ring (20).

20. The device of claim 1, wherein said valving and control mechanism (10) comprises a valve seat member (12) peripherally sealed with respect to said reservoir (3) and having a passageway extending therethrough for connecting said reservoir (3) with the flow pathway; a valve seal (26) overlaying said passageway and sealing off the reservoir (3) when said device is in said closed configuration; and a plunger (18) adapted to slide with respect to said valve seat member (12) and to compress said valve seal (26) against said valve seat member (12) to seal off the reservoir (3) when said valving and control mechanism (10) is in said closed configuration; and wherein, upon pulling said plunger (18) away from said valve seal (26), said valve seal (26) opens said flow path to said reservoir (3) wherein said valving and control mechanism (10) assumes the open configuration.

21. The device of claim 20, further comprising an upper ring (20) fitted within said housing (2), said plunger (18) being slidably positioned within said upper ring (20) and said flow path extending between said housing (2) and said upper ring (20).

22. The device of claim 21, wherein said flow path spirals around said upper ring (20).

23. The device of claim 20, wherein said plunger (18) is pulled away by translating said plunger (18).

24. The device of claim 20, wherein said plunger (18) is pulled away by rotating said plunger (18).

25. The device of claim 1, wherein said valve seat member (12) is peripherally sealed with respect to said reservoir (3) and has a passageway connecting said reservoir (3) with a peripheral opening in said valve seat member (12), said valving and control mechanism (1) comprises a top ring (20) surrounding a top portion of said valve seat member (12) and fitted within said housing (2), and said valve seat member (12) is rotatable with respect to said top ring (20), said top ring (20) further having an opening extending through a wall thereof and connecting with said flow path extending between said top ring (20) and said housing (2); and further wherein, upon rotation of said valve seat member (12) so that said valving and control mechanism assumes said open configuration, said peripheral opening aligns with said opening extending through the wall of said top ring (20), thereby connecting said reservoir (3) with said flow path.

26. The device of claim 1, wherein said valving and control mechanism (10) comprises a cap (34) arranged for rotation with respect to said valve seat member (12), said valve seat member (12) having a bore (12f) fluidly connecting said reservoir (3) with said cap (34) and a peripheral opening (12j) fluidly connecting said cap with said flow path; said cap (34) having a passageway (34a, 34b) fluidly connecting with said bore (12f) and extending peripherally out of said cap (34), wherein, upon rotation of said cap (34) so that said valving and control mechanism (10) assumes said open configuration, said passageway (34b) aligns with said peripheral opening (12j), thereby connecting said reservoir (3) with said flow path.

* * * * *